United States Patent [19]

Mann

[11] Patent Number: 5,550,113
[45] Date of Patent: Aug. 27, 1996

[54] BLOOD SUGAR REGULATING COMPOSITION AND METHODS RELATING THERETO

[76] Inventor: Morris A. Mann, 21663 W. 57th Ave., Glendale, Ariz. 85308

[21] Appl. No.: 277,875

[22] Filed: Jul. 20, 1994

[51] Int. Cl.$^6$ ............................ A61K 31/715; C08B 37/18
[52] U.S. Cl. ........................... 514/54; 514/506; 424/639; 424/646; 424/655; 536/123.1
[58] Field of Search ..................... 514/54, 506; 424/639, 424/646, 655; 536/123.1

[56] References Cited

U.S. PATENT DOCUMENTS

| | | | |
|---|---|---|---|
| 4,840,939 | 6/1989 | Leveen et al. | 514/25 |
| 5,164,384 | 11/1992 | Paul | 514/188 |
| 5,169,671 | 12/1992 | Harada et al. | 426/658 |
| 5,221,668 | 6/1993 | Henningfield et al. | 514/23 |
| 5,300,596 | 4/1994 | McNeill et al. | 514/186 |
| 5,308,627 | 5/1994 | Umbdenstock, Jr. | 424/639 |
| 5,422,346 | 6/1995 | Mitchell et al. | 514/54 |

FOREIGN PATENT DOCUMENTS

| | | |
|---|---|---|
| 59-112922 | 6/1984 | Japan . |
| 4-008270 | 1/1992 | Japan . |

OTHER PUBLICATIONS

F. A. Cotton and G. Wilkinson "Advanced Inorganic Chemistry" Fifth Edition, John Wiley & Sons, New York, 1988, pp. 625–627.

*Primary Examiner*—Gary L. Kunz
*Assistant Examiner*—Kathleen K. Fonda
*Attorney, Agent, or Firm*—Seed and Berry LLP

[57] ABSTRACT

There are disclosed compositions which, when administered to a warm-blooded animal, are capable of regulating blood sugar levels. The compositions contain inulin, one or more metal complexes, and, optionally, one or more medium chain triglycerides. Also disclosed is a method for regulating blood sugar levels by administration of the compositions of this invention.

21 Claims, 5 Drawing Sheets

BLOOD SUGAR REGULATING COMPOSITION AND METHODS RELATING THERETO

TECHNICAL FIELD

This invention relates generally to inulin-containing compositions and, more specifically, to inulin compositions which regulate blood sugar levels and decrease tendencies towards either hypoglycemia or hyperglycemia, thus decreasing tendencies towards anxiety, depression, and/or anger.

BACKGROUND OF THE INVENTION

Although not well understood, a complex relationship is known to exist between blood sugar, hormonal and nutrient status, and a person's mood. Blood sugar is modulated primarily by pancreatic and adrenal hormones. These hormones include: insulin, glucagon, epinephrine, norepinephrine, cortisone, and the various sex steroids (i.e., estrogen, progesterone, testosterone). Insulin and glucagon regulate blood sugar by either increasing glycogen or allowing the presence of free glucose for tissue consumption. It is known that certain physiologically defined disease states (e.g., diabetes mellitus (sustained hyperglycemia) and reactive or insulinoma induced hypoglycemia) are associated with specific and characteristic alterations in mood. Premenstrual syndrome and menstruation are also associated with alterations in blood sugar regulating capacity, causing, in some cases, pathological anxiety and anger among other emotions. It is likewise known that males or females taking excessive amounts of anabolic steroids are prone to irrational outbursts of aggression and rage.

Mood, defined as the predominant emotion of a given person at a given time, can be affected exogenously and endogenously. Exogenous factors include the person's particular life circumstances (e.g., incarceration may lead to the feeling of depression). In general, there is a cause and effect relationship between exogenous factors and mood. Endogenous factors that affect mood include hormonal factors, presence or absence of pain, nutrient status (including vitamins, minerals, and calories), and levels of oxygen, carbon dioxide, and other gases that are respired, as well as the relative atmospheric pressure.

Numerous medications currently exist that are used to regulate mood. These mood regulators include narcotics, stimulants, alcohol, major and minor tranquilizers, and antidepressants. Each of these medications have significant and undesirable side effects. Moreover, these medications, while ameliorating the symptoms of mood disturbance, do not treat the underlying cause. In a high percentage of cases, the cause of mood disturbances are believed to result from fluctuations in cerebral blood sugar.

Accordingly, there is a need in the art for a blood sugar regulating composition that will affect mood without the attendant side effects associated with psychoactive substances currently used for this purpose. This invention fulfills these needs, and provides other related advantages.

SUMMARY OF THE INVENTION

Briefly stated, in one embodiment, the present invention discloses compositions comprising inulin and one or more metal complexes, including (but not limited to) vanadium, chromium, and manganese complexes. In another embodiment, the compositions of this invention further comprise one or more medium chain triglycerides.

In a further embodiment, the present invention discloses a method for blood sugar regulation by systemic administration of an effective amount of the compositions of the present invention to warm-blooded animals (including humans). In yet another embodiment, a method for stabilizing the mood of warm-blooded animals by administration of the compositions is also disclosed.

Other aspects of this invention will become apparent upon reference to the following detailed description and attached drawings.

DETAILED DESCRIPTION OF THE INVENTION

Figure 1:
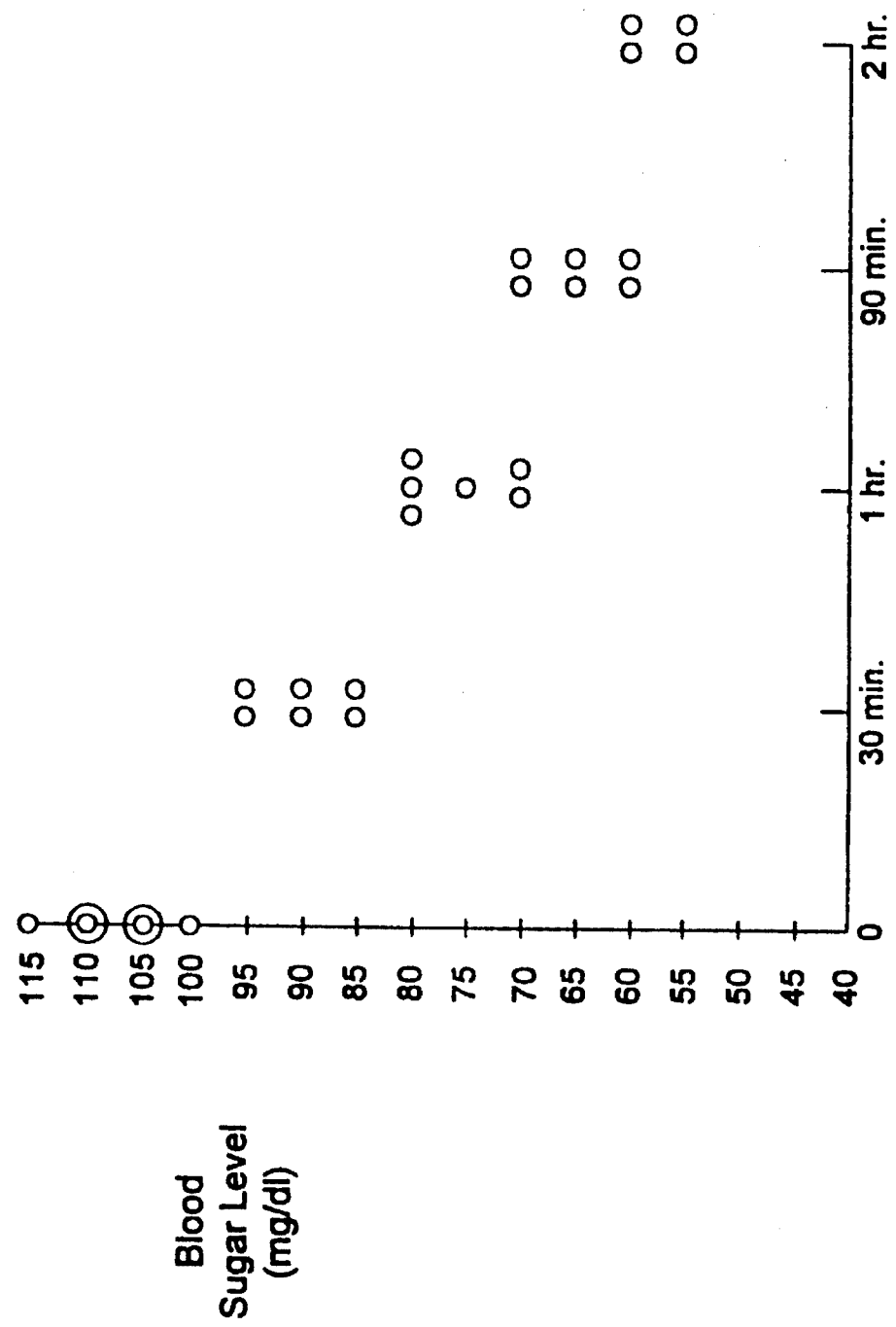
FIG. 1 illustrates the effect of exercise on blood sugar levels of subjects who were not administered a representative composition of the present invention.

The present invention is generally directed to mood stabilization through blood sugar regulation, and compositions and methods relating thereto. The compositions of the present invention include inulin, one or more metal complexes, and, optionally, one or more medium chain triglycerides. Such compositions are administered to warm-blooded animals in need thereof in an amount sufficient to regulate blood sugar level and/or stabilize the mood of the animal.

As mentioned above, the compositions of the present invention contain inulin. Inulin is a non-absorbable, non-nutritive carbohydrate that may be derived from dahlia tubers, Jerusalem artichoke, or chicory root. Inulin is a complex carbohydrate consisting of beta-linked fructose subunits that may be represented by the formula $(C_6H_{12}O_5)_n$ where n represents the number of fructose subunits in the carbohydrate and is indicative of the degree of polymerization. In the practice of the present invention, inulin with a degree of polymerization between 8 and 65 is preferred. In a more preferred embodiment, the inulin has a degree of polymerization between 15 and 30. Inulin is present in the compositions of this invention in an amount ranging from 10 to 99 percent by weight of the total composition, and preferably from 30 to 99 percent by weight of the total composition.

Prior to the isolation and purification of insulin, inulin was historically used by physicians to regulate blood sugar levels in diabetic patients. To achieve a modicum of therapeutic regulation, a dosage of between 25 and 50 grams per day of inulin was required. These exceedingly large dosages have effectively precluded the usefulness of inulin administration for blood sugar regulation. However, the inulin compositions of the present invention are effective in regulating blood sugar levels at significantly lower dosages by virtue of the apparent synergistic effect of the other non-inulin composition components (e.g., the metal complexes). In the practice of the present invention, the dosage of inulin needed to effect blood sugar regulation ranges from about 50 micrograms (ug) to no more than about 10 grams of inulin per subject per day, and preferably from about 1 gram to about 5 gram of inulin per subject per day.

Although not intending to be limited to the following theory, inulin, as a component of the compositions of the present invention, serves to regulate blood sugar levels preventing hyperglycemia and thereby decreasing insulin production in response to the ingestion of food. Accordingly, administration of the compositions of the present invention concomitantly reduce or eliminate the hyperglycemia often associated with insulin spikes which, in turn, are believed to adversely affect mood (see, e.g., *Comprehensive Textbook of Psychiatry*, Kaplan, Freedman and Sadock, ed., Williams and Wilkins, pub., Baltimore, Md.).

As mentioned above, the inulin compositions of the present invention include one or more metal complexes. The metal complex is present in the composition in an amount ranging from 0.01 to 20 percent by weight of the total composition, and preferably from 0.01 to 5 percent by weight of the total composition. These metal complexes, in conjunction with inulin, effect blood sugar regulation. Suitable metal complexes include metal complexes of chromium, manganese, and vanadium. As used herein, the term "complex" refers to any organic or inorganic ligated metal species.

While metal complexes alone generally have at least some capacity to effect blood sugar levels and improve glucose tolerance, the combination of inulin (in the amount disclosed above) and the metal complexes provide a composition which effects blood sugar level regulation significantly greater and at a much lower concentration than administration of either inulin or the individual metal complexes alone. Thus, the metal complexes are essential components of the compositions of the present invention.

For example, chromium is known to have some effect on glucose metabolism. The effect of chromium on glucose metabolism was recognized as early as 1929 with the discovery that yeast extracts potentiated the effect of insulin. Subsequently, it has been shown that chromium supplementation improved glucose tolerance in humans. Since then, several U.S. patents have disclosed the ability of chromium picolinate to influence blood sugar and insulin output (U.S. Pat. Nos. 5,164,384 and 4,315,927). In addition, it has been determined that the ability of mammalian tissue to absorb chromium decreases with age (see, e.g., Schroeder, *The Trace Elements and Man*, Devin-Adair, pub., Old Greenwich, Conn., 1977), and may explain, in part, maturity onset diabetes and its prevalence in humans after the age of 50.

Furthermore, some chromium complexes are known to have biological activity, including chromium trichloride, chromium acetate, chromium nicotinate (the active component of the metallovitamin, Glucose Tolerance Factor, isolated from yeast), chromium picolinate, chromium glycinate, chromium oxalate, chromium perchlorate, chromium salicylate, and chromium-4-oxo-pyridine-2,6-dicarboxylate. Chromium is also a dietary requirement and chromium dietary requirements in humans range from about 50 to 200 ug per day.

Like chromium, manganese also improves glucose tolerance. Historically, glucose intolerance resulting from manganese deficiency was demonstrated in 1958. More recently, the importance of manganese in the diets of humans was demonstrated by Schroeder in 1966 (Schroeder et al., *J. Chronic Diseases* 19:545–71, 1966). Although not formally listed as a required nutrient, manganese requirements in humans have been determined to be between 3 and 4 mg per day. Although manganese is poorly absorbed, the ability to absorb manganese does not decrease with age. The dietary dosage of manganese ranges from 2 to 100 mg per day.

Vanadium also effects blood sugar regulation and has recently been classified as an essential trace mineral. Vanadium complexes have been used in therapeutic applications including the treatment of diabetes. Vanadium is poorly absorbed and dietary intake ranges from about 2 to 15 mg per day. Because vanadium is poorly absorbed and its numerous complexes are extremely toxic, few vanadium complexes have been demonstrated to possess biological activity.

The chromium complexes of the present invention include organic and inorganic chromium complexes such as chromium acetate, chromium chloride, chromium potassium oxalate, and chromium potassium sulfate. In a preferred embodiment, the chromium complex is chromium picolinate. In a particularly preferred embodiment, the chromium complex is chromium-4-oxo-pyridine-2,6-dicarboxylate.

The manganese complexes of the present invention include manganese acetate, manganese chloride, manganese carbonate, potassium permanganate, dimanganese trisulphate, manganese gluconate, manganese glycinate and manganese citrate. In a preferred embodiment, the manganese complex is manganese gluconate or manganese glycinate.

Like the chromium complexes, the vanadium complexes include organic and inorganic vanadium complexes such as vanadium carbonyl, vanadium pentoxide, vanadium trisulfate, vanadyl dichloride, and vanadyl trichloride. Various organic vanadium complexes may also used in the composition of the present invention. Examples of organic vanadium complexes include vanadyl glycinate, vanadyl gluconate, and vanadyl citrate. In a preferred embodiment, the vanadium complex is vanadyl sulfate ($VSO_5$).

The compositions of the present invention optionally include medium chain triglycerides. As used herein, the term "medium chain triglyceride" ("MCT") refers to a triester of glycerol containing medium length chain carboxylic acids. Medium length chain carboxylic acid chains are $C_6$ to $C_{12}$ carboxylic acids. The three medium chain carboxylic acids that are attached to the triglyceride backbone of the MCT may be, but need not be, the same. The medium chain carboxylic acids can be either saturated or unsaturated, but are preferably saturated. Examples of medium chain carboxylic acids of this invention include $C_6$ (caproic acid), $C_8$ (caprylic acid), $C_{10}$ (capric acid), and $C_{12}$ (lauric acid). As mentioned above, the MCT may bear one or more different carboxylic acid chains. In preferred embodiments, the MCTs comprise a mixture of from about 60% $C_8$ and about 40% $C_{10}$ to a mixture of about 80% $C_8$ and about 20% $C_{10}$. Odd numbered chains, such as $C_7$, $C_9$, and $C_{11}$ fatty acids, are less common, but are included within the scope of this invention. Further, the MCTs of the present invention may include minor amounts of short or long chain fatty acids. The medium chain triglycerides are used in the present invention to reduce cravings for simple sugars which would otherwise increase insulin secretion. The medium chain triglyceride is optionally present in the composition in an amount ranging from 0 to 90 percent by weight of the total composition, and preferably from 0 to 67 percent by weight of the total composition.

As will be described below in more detail, the compositions of the present invention may be administered to warm-blooded animals to effect blood sugar regulation, and also have the beneficial effect of mood stabilization. The compositions of this invention also have a further beneficial effect of suppressing appetite, thereby facilitating weight loss.

The compositions of the present invention may be administered systemically. Accordingly, the compositions may be formulated for oral as well as injectable administration. In the case of oral administration, the compositions of this invention may be manufactured by combining all ingredients in a form suitable for oral administration, and preferably as a capsule or tablet. For example, the compositions of the present invention may be encapsulated (such as in a coating of hard gelatin) for oral administration. Such techniques are well known in the art (see, e.g., Baker, Richard, *Controlled Release of Biologically Active Agents*, John Wiley & Sons, 1986). Inert fillers may also be present in the oral (e.g., tablet or capsule) form. Suitable inert fillers include magnesium stearate and silicon dioxide. The inert fillers may be present in the compositions of the invention up to less than 3 percent by weight of the total composition.

Alternatively, the compositions may first be combined with one or more suitable carriers or diluents to yield a pharmaceutical preparation suitable for oral or parenteral application. Such diluents or carriers, however, should not interact with the mood stabilizing compositions to significantly reduce the effectiveness thereof. Suitable carriers for parenteral application (such as intravenous, subcutaneous or intramuscular injection) include sterile water, physiological saline, bacteriostatic saline (saline containing 0.9 mg/ml benzyl alcohol) and phosphate-buffered saline. Effective administration will preferably deliver an inulin dosage of from about 50 micrograms to about 10 grams per day. Representative examples of mood stabilizing compositions of this invention are presented in Examples 1 and 2.

In another aspect of the present invention, a method for regulating blood sugar levels is disclosed. The method provides for the systemic administration of the compositions of the present invention in a quantity sufficient to regulate blood sugar levels in warm-blooded animals. In one embodiment, the compositions of the present invention are administered to a warm-blooded animal in an oral form. When formulated as capsules, the inulin composition is preferably administered one to three times a day. While the oral dosage may contain from 100 mg to 6000 mg (i.e., total weight of all active ingredients), a single tablet or capsule containing more than about 1000 mg may be too large to easily swallow. Thus, the composition may be administered in either multiple capsule or multiple tablet form. In addition, the total weight of all active ingredients will depend on the form of ingredients used.

The efficacy of the compositions of the present invention in regulating blood sugar levels in humans is presented in Examples 3 and 4, respectively. Example 3 demonstrates the efficacy of representative compositions in maintaining blood sugar levels in subjects during aerobic exercise. Example 4 demonstrates the efficacy of representative compositions in regulating blood sugar levels in diabetic patients in response to glucose challenge.

In a further aspect of this invention, a method for stabilizing mood is disclosed. This method provides for the systemic administration of the compositions of the present invention in a quantity sufficient to stabilize mood in warm-blooded animals. In one embodiment, the compositions are orally administered to warm-blooded animals. The oral administration of a composition of the present invention for mood stabilization is described in more detail in Example 5.

In yet another aspect of the present invention, a method for suppressing appetite and thereby facilitating weight loss is also disclosed. This method provides for the systemic administration of the compositions of the present invention in a quantity sufficient to suppress appetite and facilitate weight loss in warm-blooded animals. In one embodiment, the compositions are administered orally. The efficacy of representative compositions for appetite suppression and weight loss is presented in Example 6.

The following examples are provided for the purposes of illustration and are not intended to be limiting.

EXAMPLES

The sources for the ingredients for the formulations below are as follows: Inulin (California Natural Products, Lathrop, Calif.); Chromium picolinate, Chromium-4 -oxo-pyridine-2,6-dicarboxylate, Manganese gluconate, vanadyl sulfate (Thorne Research, Sand Point, Id.); Medium chain triglyceride (75% $C_8$, 25% $C_{10}$), (Henkel, Chicago, Ill.).

Example 1

Representative Compositions

Capsule formulations of representative compositions containing inulin and one or more metal complexes were made by powdering the following ingredients and then encapsulating:

| Formulation A | |
| --- | --- |
| Inulin | 400 mg |
| Chromium picolinate | 200 ug |
| Vanadyl sulfate | 3 mg |
| Formulation B | |
| Inulin | 400 mg |
| Chromium picolinate | 200 ug |
| Manganese gluconate | 15 mg |

Example 2

Representative Compositions Containing Medium Chain Triglycerides

Capsule formulations of representative compositions containing inulin, one or more metal complexes, and a medium chain triglyceride (MCT) were made by powdering the following ingredients and then encapsulating:

| Formulation C | |
| --- | --- |
| Inulin | 200 mg |
| MCT | 400 mg |
| Chromium picolinate | 200 ug |

-continued

| Formulation D | |
|---|---|
| Inulin | 400 mg |
| MCT | 200 mg |
| Chromium picolinate | 200 ug |
| Vanadyl sulfate | 3 mg |
| Formulation E | |
| Inulin | 200 mg |
| MCT | 400 mg |
| Chromium-4-oxo-pyridine-2,6-dicarboxylate | 200 ug |
| Formulation F | |
| Inulin | 200 mg |
| MCT | 400 mg |
| Manganese gluconate | 15 mg |
| Chromium-4-oxo-pyridine-2,6-dicarboxylate | 200 ug |

Example 3

Evaluation of Representative Compositions to Assess Their Ability to Stabilize Blood Sugar Levels During Aerobic Exercise The efficacy of a representative composition of the present invention to stabilize blood sugar was evaluated through an exercise protocol. It is well known that progressive aerobic exercise lowers blood sugar levels. A baseline study was first performed with six male, well trained athletes. Each subject was hydrated prior to initiation of the exercise, and neither food nor drink was permitted after the commencement of the exercise.

The exercise comprised an aerobic workout for 2 hours on a Cybex Exercise Ergometer (Lumex, Inc., Ronkonkoma, N.Y.) set at 205 watts. In such an exercise, the amount of work that each subject was required to perform was maintained at 205 watts throughout the test's duration. Finger prick blood glucose measurements were done immediately prior to exercise and thereafter at intervals of one-half hour, for a period of two hours. Eight subjects completed the test, two dropped out after 90 minutes due to dehydration. The results of this baseline study are presented graphically in FIG. 1. As shown in FIG. 1, blood sugar levels were reduced from between 100 to 115 mg/dl to about 52 to 60 mg/dl over the course of the 2 hour exercise.

The ability of the compositions of the present invention to regulate blood sugar levels was demonstrated by comparison to the exercise results described above. Immediately prior to initiation of the above-described exercise protocol, four subjects were hydrated and were administered 3 capsules of Formulation A (400 mg inulin, 200 ug chromium picolinate, 3 mg vanadyl sulfate). As before, neither food nor drink was provided after the commencement of the exercise. The blood sugar levels of these subjects is presented graphically in FIG. 2.

Figure 2:
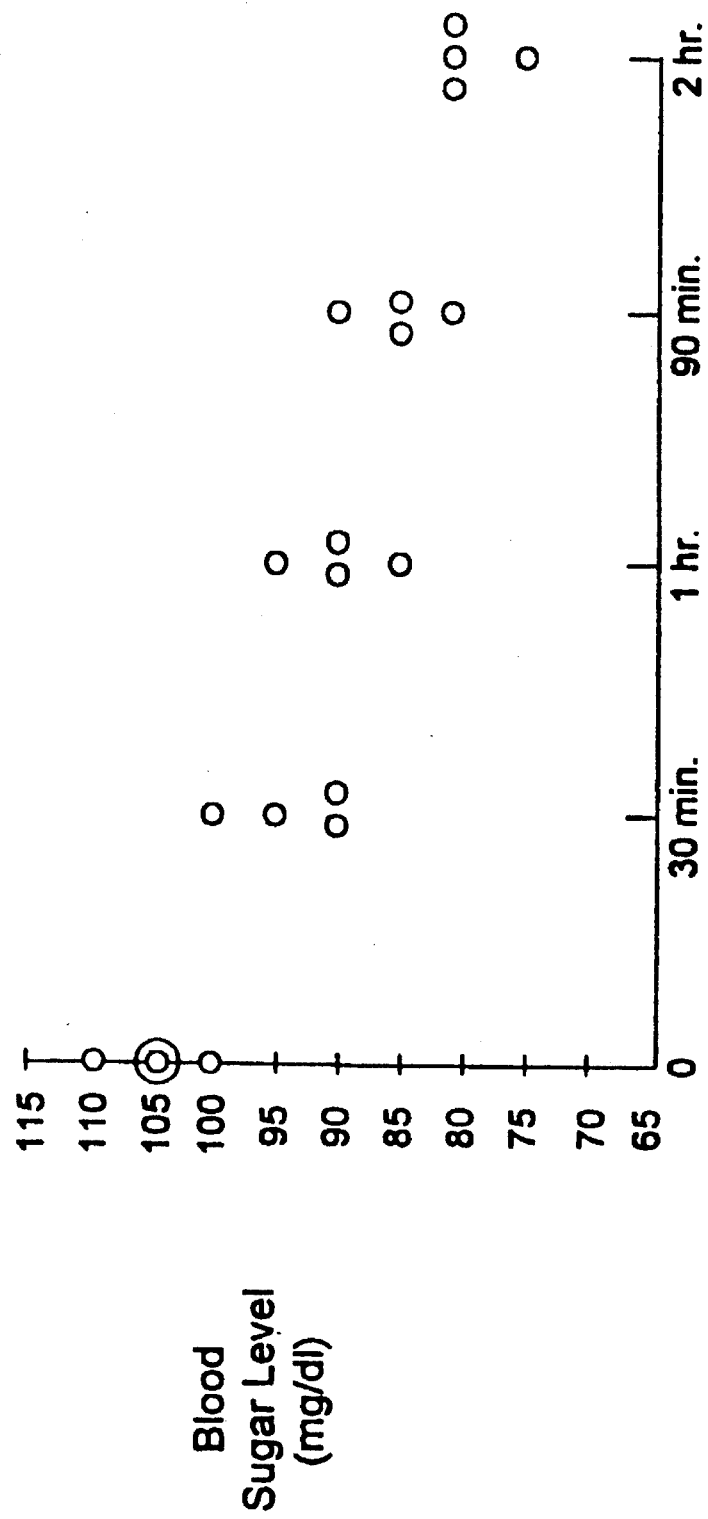
FIG. 2 illustrates the effect of exercise on blood sugar levels of subjects who were administered a representative composition of the present invention (i.e., 400 mg inulin, 200 ug chromium picolinate, 3 mg vanadyl sulfate).

As shown in FIG. 2, blood sugar levels were reduced from between 100 to 110 mg/dl to about 75 to 80 mg/dl over the course of the 2 hour exercise. In comparison to the baseline study in which the subjects of the exercise protocol were not administered a representative composition of this invention, the subjects receiving Formulation A had significantly greater blood sugar levels during and upon completion of the exercise protocol. At the end of the exercise protocol, those subjects receiving Formulation A had blood sugar levels approximately 50 percent greater than those subjects in the baseline study.

In a further study utilizing the above-mentioned exercise protocol, the effects of Formulation E on blood sugar levels was also evaluated. Four subjects were hydrated and administered 3 capsules of Formulation E (200 mg, inulin, 400 mg medium chain triglyceride, 200 ug chromium-4-oxo-pyridine-2,6-dicarboxylate). The results are shown graphically in FIG. 3.

Figure 3:
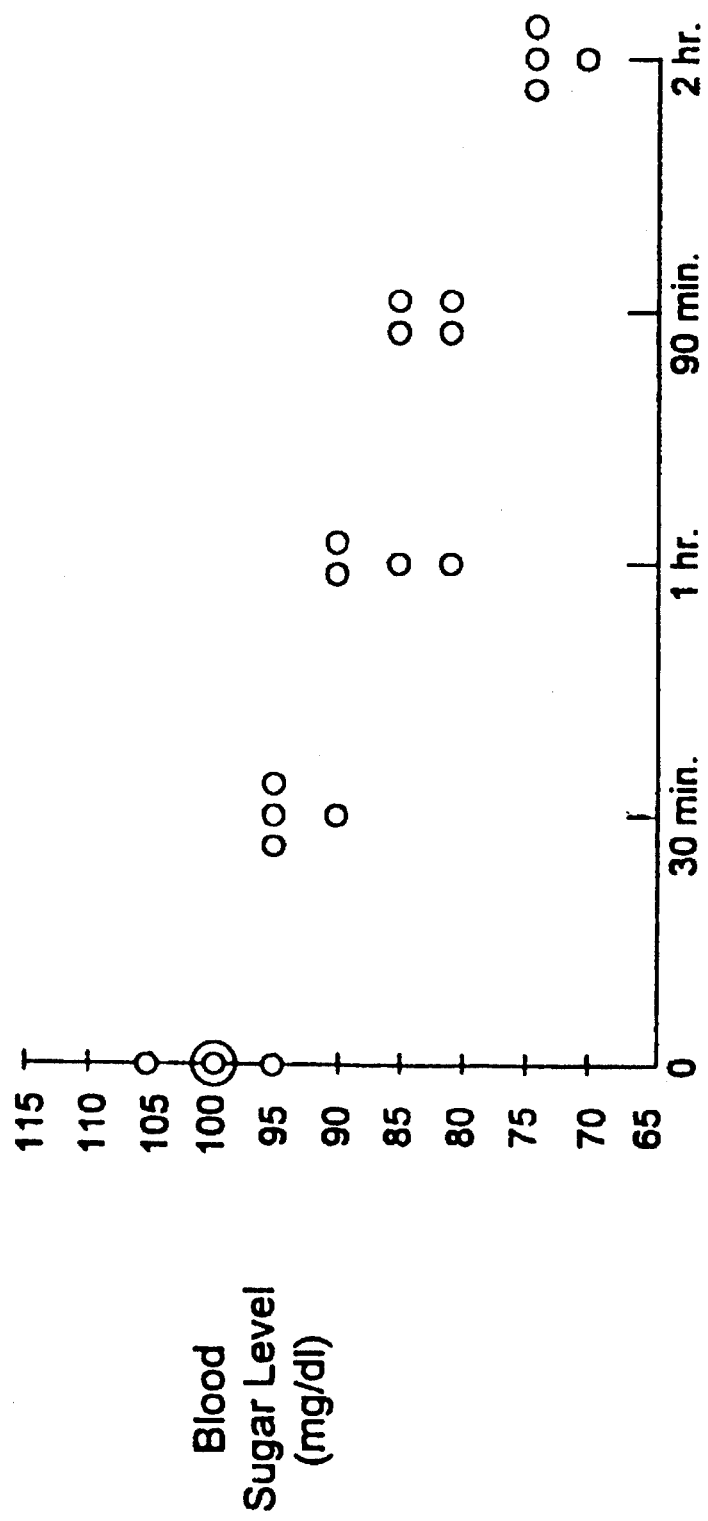
FIG. 3 illustrates the effect of exercise on blood sugar levels of subjects who were administered a representative composition of the present invention (i.e., 200 mg inulin, 400 mg medium chain triglyceride, 200 ug chromium-4-oxo-pyridine-2,6-dicarboxylate).

As shown in FIG. 3, blood sugar levels decreased from between 95 to 105 mg/dl to about 70 to 75 mg/dl as a result of the exercise. These results indicate that, like Formulation A, Formulation E is also effective in maintaining an elevated blood sugar level in subjects receiving representative compositions of the present invention relative to those subjects receiving no supplements.

Example 4

Evaluation of Representative Compositions to Assess Their Ability in Stabilizing Blood Sugar Levels Upon Glucose Challenge To evaluate the ability of the compositions of the present invention to stabilize blood sugar levels upon glucose challenge, Formulation A was administered to four individuals with insulin dependent diabetes mellitus and two individuals with definitive reactive hypoglycemia. The individuals with reactive hypoglycemia developed blood sugar levels of 40 and 32 mg/dl, respectively, within 90 minutes when challenged with a 100 gram glucose load.

Formulation A was administered to the individuals with diabetes mellitus (5 capsules, 3 times daily for one month). In all cases, the insulin requirements as determined by blood sugar analysis were greatly diminished (i.e., 25% or more reduction of insulin use). Two individuals were able to decrease their insulin administration to once daily.

Likewise, the two individuals with reactive hypoglycemia who received Formulation A (2 capsules, 3 times daily for one month) did not experience signs or symptoms of hypoglycemia. In addition, blood sugar analysis showed that even 1.5 hours after meals, their blood sugar level never dropped below 80 mg/dl.

Furthermore, all subjects involved in the study noticed mood stabilization. The diabetics noted a marked reduction in feelings of anxiety and depression. The reactive hypoglycemics reported experiencing less anger and fewer mood swings (e.g., elation followed by depression).

Example 5

Evaluation of a Representative Composition by the Hamilton Anxiety Test

Representative compositions of the present invention were evaluated for their ability to stabilize mood utilizing the Hamilton Anxiety Rating Scale (see, e.g., *Comprehensive Textbook of Psychiatry*, Kaplan, Freedman and Sadock, ed., Williams and Wilkins, pub., Baltimore, Md.). In the Hamilton Anxiety Rating, a score of 0–10 is within normal limits, 10–20 indicates a potential need for counseling or other intervention, and 20 and above indicates a potential need for pharmaceutical intervention. Ten patients were interviewed by a board certified psychiatrist. Thereafter, the patients were given 120 capsules of Formulation A. The patients were instructed to take 2–3 capsules twice a day.

Following 30 days, the patients were reevaluated. The results of the experiment (i.e., diagnoses and Hamilton scores) are presented in the following Table.

TABLE

| Patient | Diagnosis | Before | After |
|---|---|---|---|
| One | Clinical depression | 23 | 14 |
| Two | Severe premenstrual syndrome | 19 | 11 |
| Three | Anxiety, depression, obesity | 26 | 16 |
| Four | Severe depression, reactive hypoglycemia | 24 | 10 |
| Five | Anxiety, menopause | 22 | 12 |
| Six | Gilles de la Tourette syndrome | 34 | 22 |
| Seven | Depression, premenstrual syndrome | 21 | 9 |
| Eight | Anxiety, reactive hypoglycemia | 24 | 8 |
| Nine | Depression, adult onset diabetes mellitus* | 19 | 10 |
| Ten | Depression, facial tics | 26 | 14 |

*This patient was able to discontinue his oral hypoglycemic agent three weeks into the study.

Formulation A was most effective in stabilizing mood for those patients suffering from premenstrual syndrome. These patients all noted an absence of symptoms in the week prior to menstruation. The patient with Gilles de la Tourette syndrome (a neuropsychiatric abnormality characterized by facial and body tics, and inappropriate, often obscene utterances) noted a significant decrease in body tics and less inappropriate speech although he continued to take his specifically prescribed medication. The patient with menopause had severe hot flashes and diaphoresis which was initially greatly diminished, and by week four was no longer a problem. Anxiety and depression, which were presenting complaints in several of the patients, were greatly diminished throughout the course of the study.

Example 6

The Effect of Representative Compositions on Appetite and Weight Loss

Figure 4:
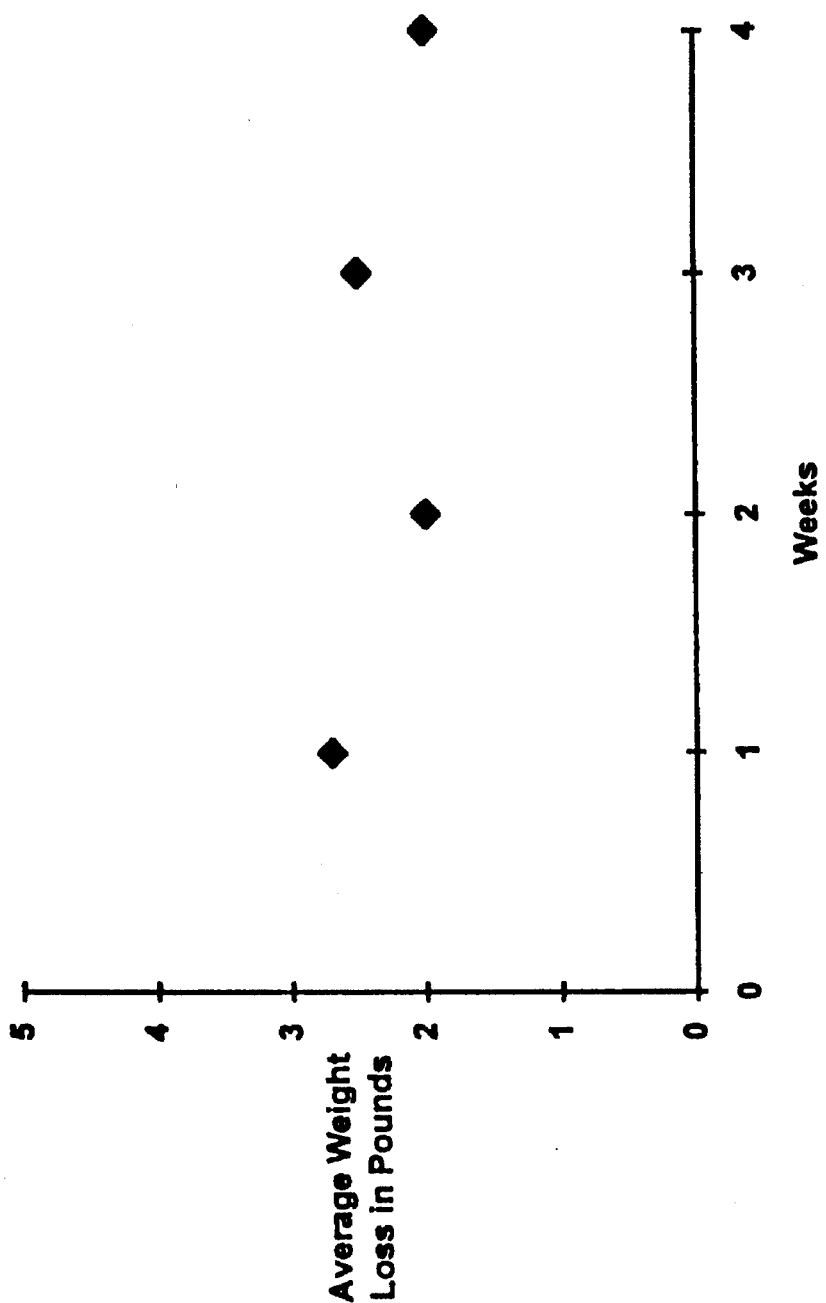
FIG. 4 illustrates the weight loss effect on subjects who were administered a representative composition of the present invention (i.e., 400 mg inulin, 200 ug chromium picolinate, 3 mg vanadyl sulfate).
Figure 5:
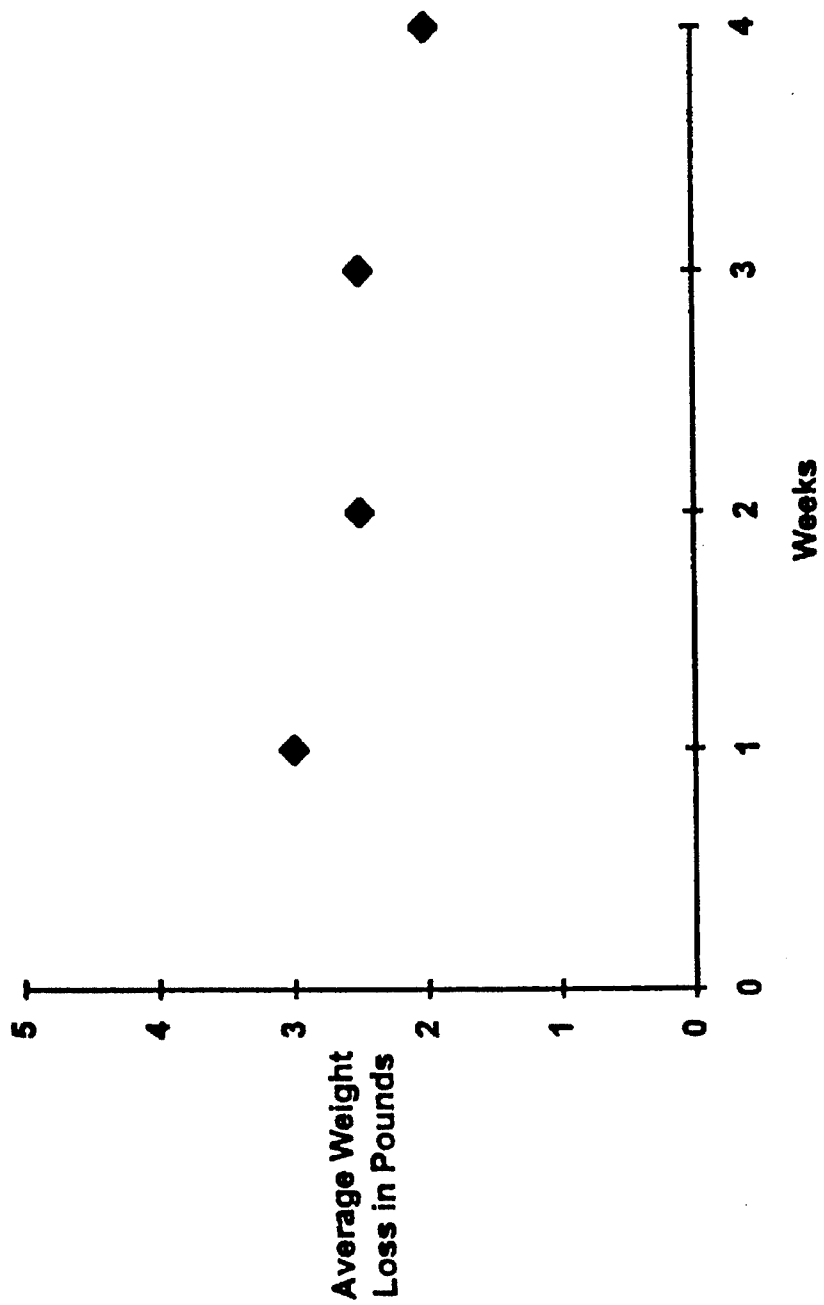
FIG. 5 illustrates the weight loss effect on subjects who were administered a representative composition of the present invention (i.e., 200 mg inulin, 400 mg medium chain, 200 ug chromium-4-oxo-pyridine-2,6-dicarboxylate).

Effect on appetite and attendant weight loss were noted with chronic administration of a representative composition for more than two weeks. Twenty individuals were administered either Formulation A or Formulation E. The individuals were instructed to take the one capsule of the formulation compound at 11 a.m. and another capsule at 4 p.m. Ten individuals were given Formulation A and ten individuals were given Formulation E. All individuals were weighed weekly for one month. The weights of the individuals was summed together, divided by 10, and subtracted from the previous week's total. Average weight loss in pounds per week for Formulation A is presented graphically in FIG. 4. As shown in FIG. 4, the weight loss per week varied between about 2 and 3 pounds during the course of the 4 week study. Similar results were obtained for Formulation E and are presented graphically in FIG. 5. All subjects expressed a desire to continue using the composition.

From the foregoing description, it is evident that certain modifications and changes can be made without departing from the spirit and scope of the invention.

I claim:

1. A composition comprising inulin, a metal complex, and a pharmaceutically acceptable carrier therefor wherein the metal of the metal complex is selected from vanadium, chromium and manganese.

2. The composition of claim 1 wherein inulin has a degree of polymerization between 8 and 65.

3. The composition of claim 1 wherein the metal complex is vanadyl sulfate.

4. The composition of claim 1 wherein the metal complex is chromium picolinate.

5. The composition of claim 1 wherein the metal complex is chromium-4-oxo-pyridine-2,6-dicarboxylate.

6. The composition of claim 1 wherein the metal complex is selected from the group consisting of manganese gluconate and manganese glycinate.

7. The composition of claim 1 further comprising a medium chain triglyceride.

8. The composition of claim 7 wherein the medium chain triglyceride contains a carboxylic acid selected from the group consisting of caproic acid, caprylic acid, capric acid, and lauric acid.

9. The composition of claim 8 wherein the carboxylic acid is a mixture of 60% to 80% caprylic acid and 40% to 20% capric acid.

10. A method for regulating blood sugar level in a warm-blooded animal in need thereof, comprising administering to animal an effective amount of a composition comprising inulin, a metal complex, and a pharmaceutically acceptable carrier therefor wherein the metal of the metal complex is selected from vanadium, chromium and manganese.

11. The method of claim 10 wherein inulin is administered to the animal in a dosage ranging from 50 micrograms to 10 grams per day.

12. The method of claim 10 wherein the composition is administered orally.

13. The method of claim 10 wherein the composition is administered by injection.

14. The method of claim 10 wherein inulin has a degree of polymerization between 8 and 65.

15. The method of claim 10 wherein the metal complex is vanadyl sulfate.

16. The method of claim 10 wherein the metal complex is chromium picolinate.

17. The method of claim 10 wherein the metal complex is chromium-4-oxo-pyridine-2,6-dicarboxylate.

18. The method of claim 10 wherein the metal complex is selected from the group consisting of manganese gluconate and manganese glycinate.

19. The method of claim 10 wherein the composition further comprises a medium chain triglyceride.

20. The method of claim 19 wherein the medium chain triglyceride contains a carboxylic acid selected from the group consisting of caproic acid, caprylic acid, capric acid, and lauric acid.

21. The method of claim 20 wherein the carboxylic acid is a mixture of 60% to 80% caprylic acid and 40% to 20% capric acid.

* * * * *